(12) United States Patent
Seward et al.

(10) Patent No.: US 7,547,294 B2
(45) Date of Patent: *Jun. 16, 2009

(54) MICROFABRICATED SURGICAL DEVICE FOR INTERVENTIONAL PROCEDURES

(75) Inventors: Kirk Patrick Seward, Dublin, CA (US); Albert P. Pisano, Danville, CA (US)

(73) Assignee: The Regents of The University of California, Oakland, CA (US)

( * ) Notice: Subject to any disclaimer, the term of this patent is extended or adjusted under 35 U.S.C. 154(b) by 882 days.

This patent is subject to a terminal disclaimer.

(21) Appl. No.: 10/490,129

(22) PCT Filed: Sep. 20, 2002

(86) PCT No.: PCT/US02/29666
§ 371 (c)(1),
(2), (4) Date: Mar. 18, 2004

(87) PCT Pub. No.: WO03/024311

PCT Pub. Date: Mar. 27, 2003

(65) Prior Publication Data

US 2004/0204675 A1    Oct. 14, 2004

Related U.S. Application Data

(63) Continuation-in-part of application No. 09/961,080, filed on Sep. 20, 2001, now Pat. No. 6,547,803.

(51) Int. Cl.
*A61M 37/00* (2006.01)
*A61B 17/20* (2006.01)
*A61M 5/32* (2006.01)
*A61B 17/34* (2006.01)
*A61M 29/00* (2006.01)

(52) U.S. Cl. .......... 604/103.01; 604/22; 604/93.01; 604/95.03; 604/103.02; 604/103.14; 604/272; 606/185; 606/194

(58) Field of Classification Search .......... 604/22, 604/93.01, 95.02, 95.03, 96.01, 97.01, 97.02, 604/103, 103.01, 103.02, 103.07, 103.08, 604/103.14, 104, 271, 272, 913; 606/159, 606/167, 170, 172, 185, 190, 191, 194, 195
See application file for complete search history.

(56) References Cited

U.S. PATENT DOCUMENTS 5,112,305 A * 5/1992 Barath et al. .......... 604/103.01
(Continued)

FOREIGN PATENT DOCUMENTS

JP         5-293176         11/1993
(Continued)

OTHER PUBLICATIONS

U.S. Office Action mailed Feb. 23, 2007, from U.S. Appl. No. 10/490,191.
(Continued)

*Primary Examiner*—Kevin C Sirmons
*Assistant Examiner*—Bhisma Mehta
(74) *Attorney, Agent, or Firm*—Beyer Law Group LLP

(57) ABSTRACT

An actuator for an interventional surgical procedure is described. The actuator may include an actuator body having a distal end and a proximal end. A central expandable section is located between the distal end and the proximal end. The expandable section is operable between an unactuated condition in which the expandable section is in a furled state and an actuated condition in which the expandable section is in an unfurled state. A needle is located at the expandable section. The needle is moveable in an approximately perpendicular direction relative to a central longitudinal axis of the actuator body from a position within the actuator body to a position outside of the actuator body.

31 Claims, 7 Drawing Sheets

U.S. PATENT DOCUMENTS

| | | | |
|---|---|---|---|
| 5,196,024 A * | 3/1993 | Barath | 606/159 |
| 5,242,397 A * | 9/1993 | Barath et al. | 604/103.01 |
| 5,354,279 A | 10/1994 | Hofling | |
| 5,423,851 A | 6/1995 | Samuels | |
| 5,538,504 A | 7/1996 | Linden et al. | |
| 5,645,564 A | 7/1997 | Northrup et al. | |
| 5,681,281 A | 10/1997 | Vigil et al. | |
| 5,693,029 A | 12/1997 | Leonhardt | |
| 5,722,989 A | 3/1998 | Fitch et al. | |
| 6,009,877 A | 1/2000 | Edwards | |
| 6,059,815 A | 5/2000 | Lee et al. | |
| 6,102,904 A | 8/2000 | Vigil et al. | |
| 6,102,933 A | 8/2000 | Lee et al. | |
| 6,210,392 B1 * | 4/2001 | Vigil et al. | 604/507 |
| 6,283,947 B1 | 9/2001 | Mirzaee | |
| 6,302,870 B1 | 10/2001 | Jacobsen et al. | 604/272 |
| 6,547,803 B2 * | 4/2003 | Seward et al. | 606/185 |
| 6,860,867 B2 | 3/2005 | Seward et al. | |

FOREIGN PATENT DOCUMENTS

| | | |
|---|---|---|
| JP | 2591573 | 12/1996 |
| JP | 11-262527 | 9/1999 |
| JP | 2003-708 | 1/2003 |
| WO | WO 02/100459 | 12/2002 |

OTHER PUBLICATIONS

U.S. Office Action mailed Sep. 20, 2007, from U.S. Appl. No. 10/490,191.

U.S. Office Action mailed Jan. 14, 2004, from U.S. Appl. No. 09/961,079.

U.S. Office Action mailed Aug. 11, 2004, from U.S. Appl. No. 09/961,079.

U.S. Office Action mailed Mar. 17, 2008, from U.S. Appl. No. 10/490,191.

Office Action dated Sep. 9, 2008 from Japanese Application No. 2003-528213.

Search Report dated Sep. 18, 2008 from European Application No. 02766308.

Japanese Office Action dated Sep. 9, 2008 from Japanese Application No. 2003-528213.

* cited by examiner

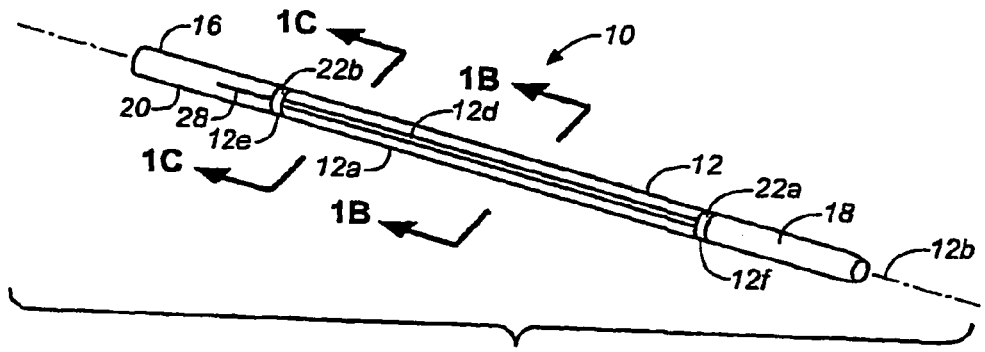
FIG._1A
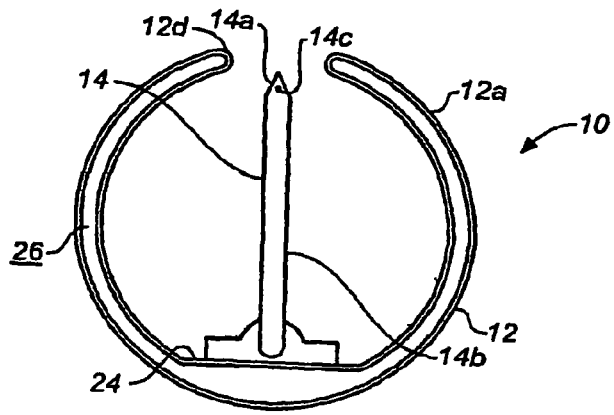
FIG._1B
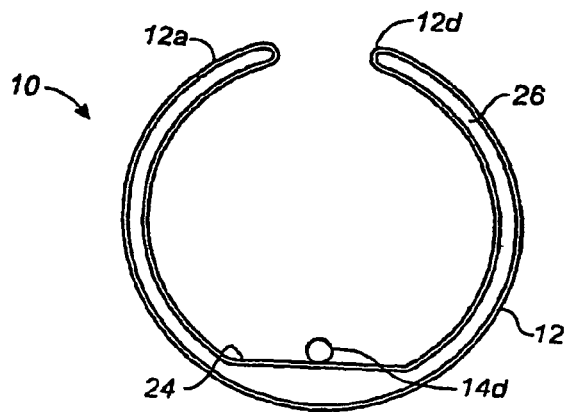
FIG._1C

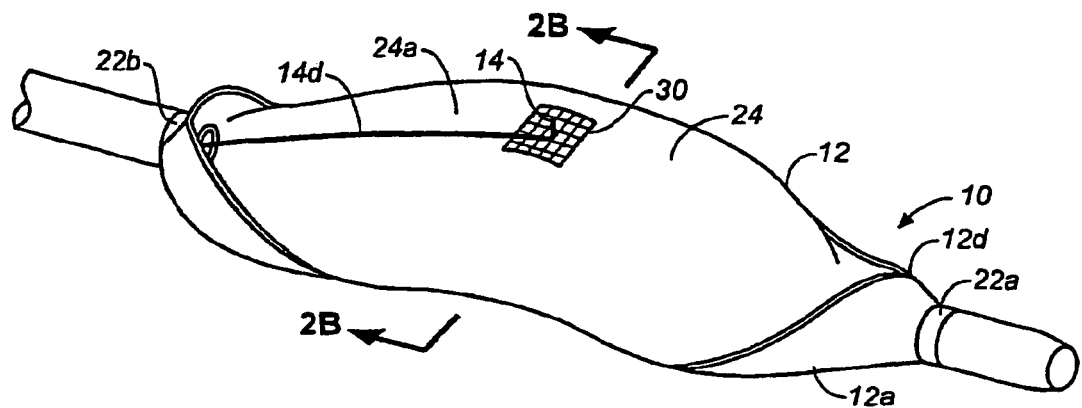
FIG._2A
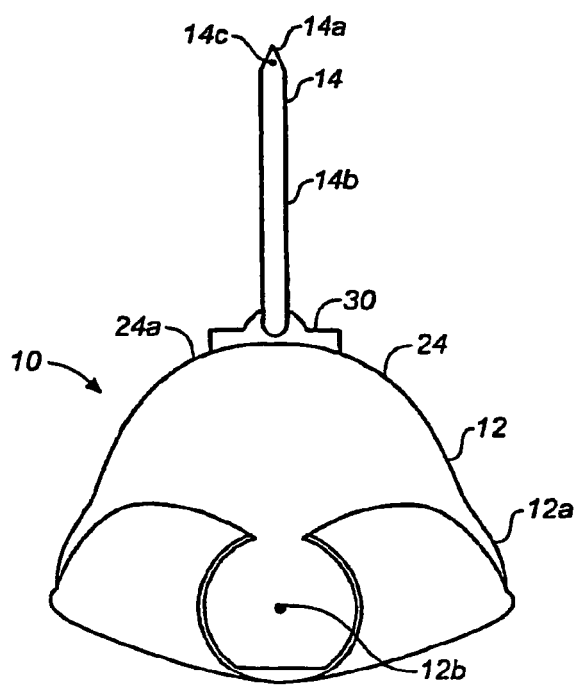
FIG._2B

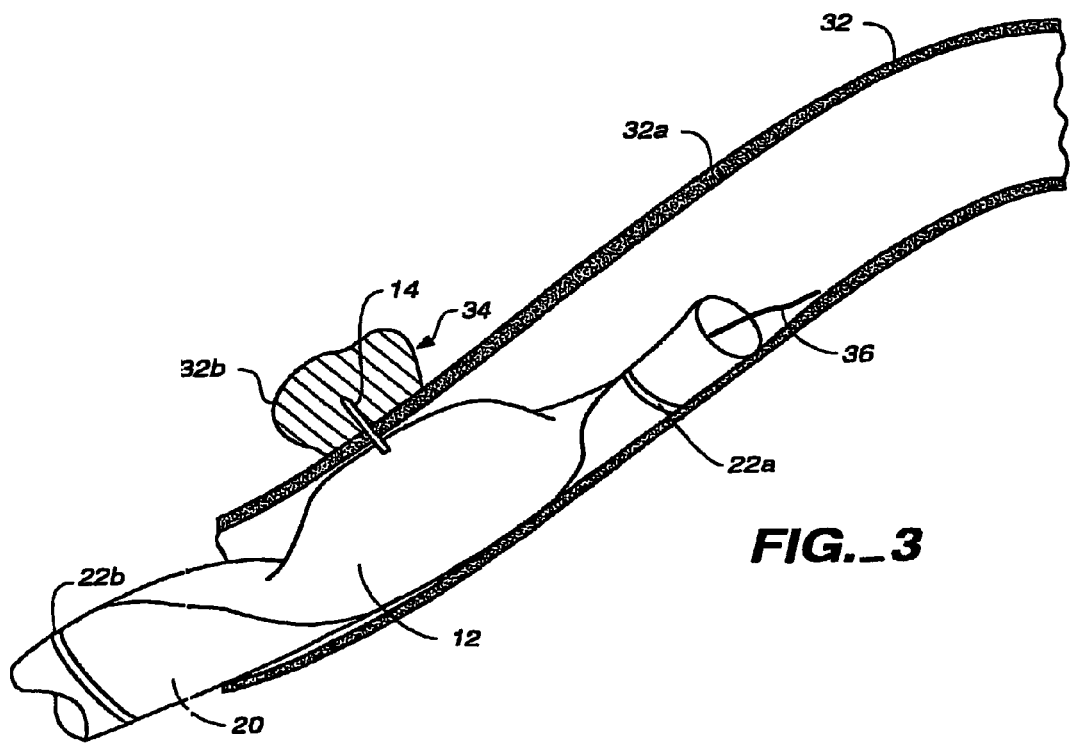
FIG._3

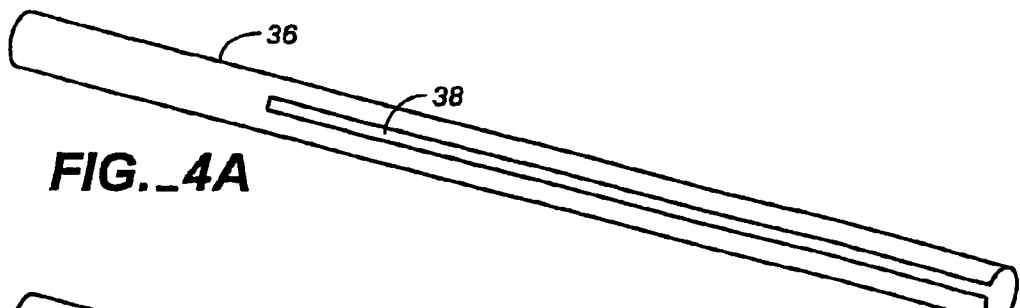
*FIG._4A*
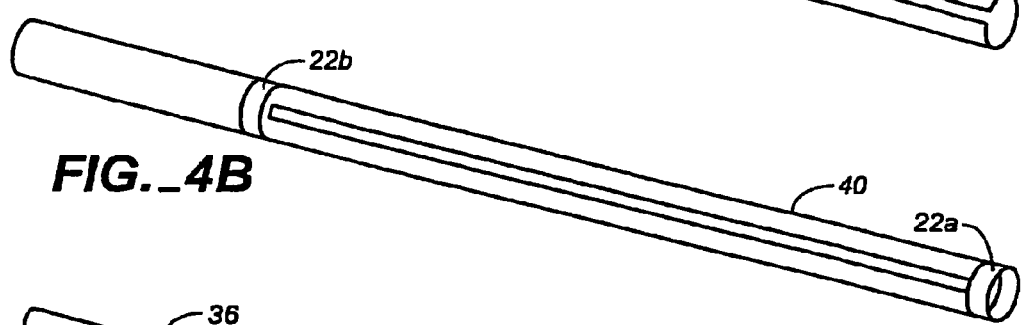
*FIG._4B*
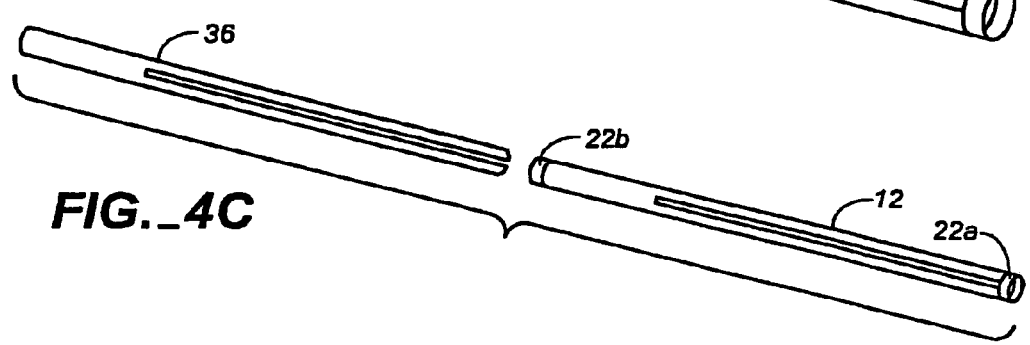
*FIG._4C*
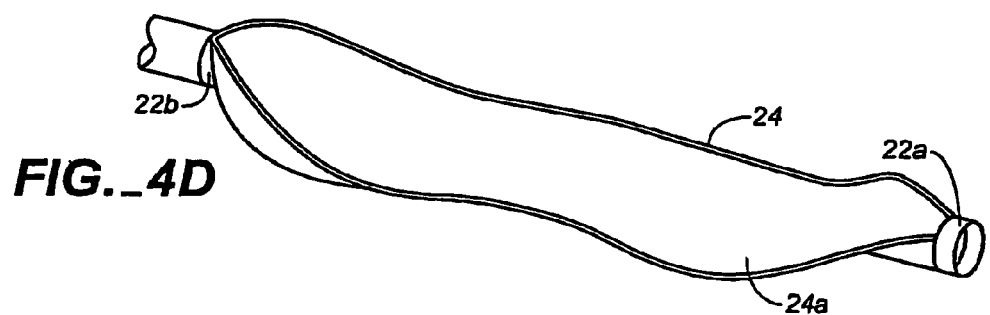
*FIG._4D*
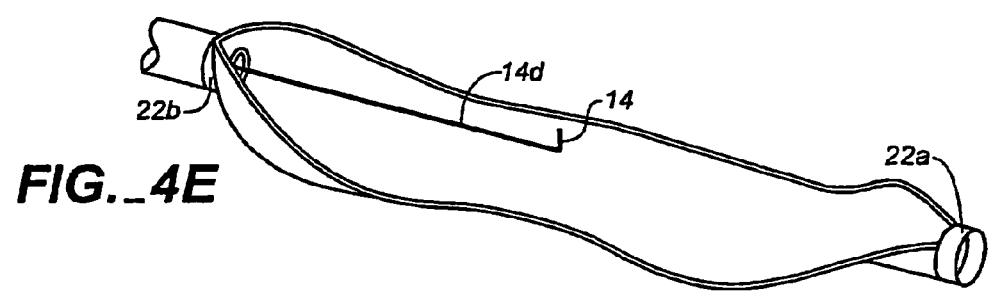
*FIG._4E*

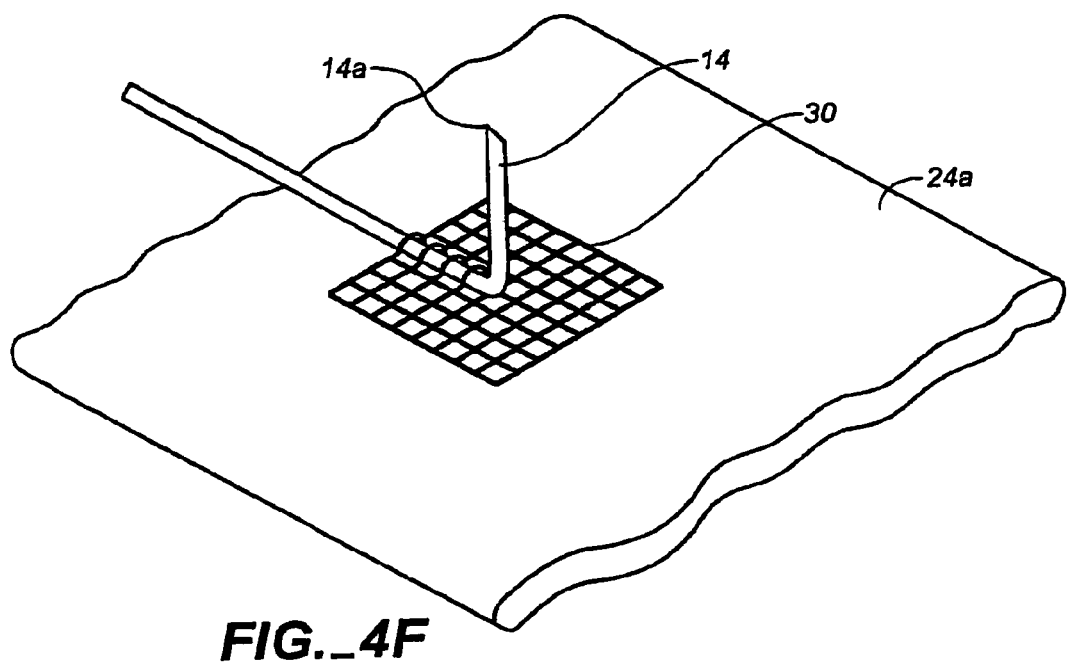
FIG._4F
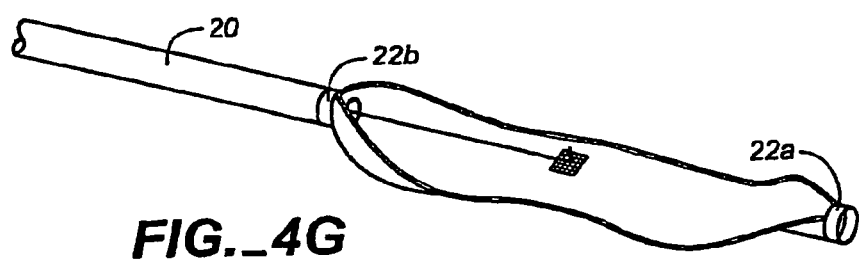
FIG._4G

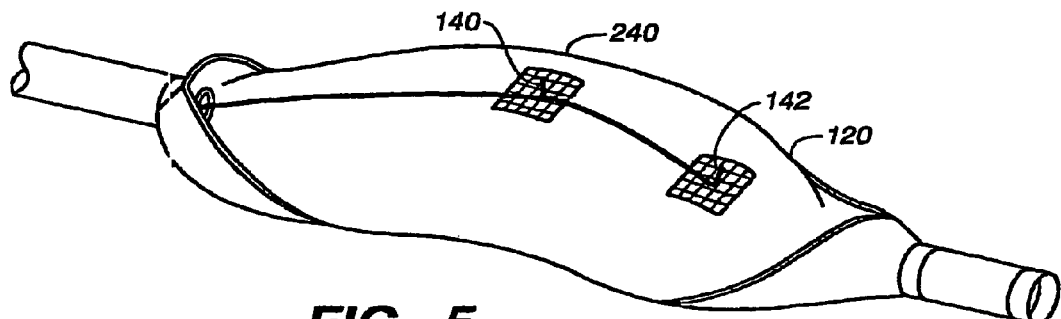
FIG._5
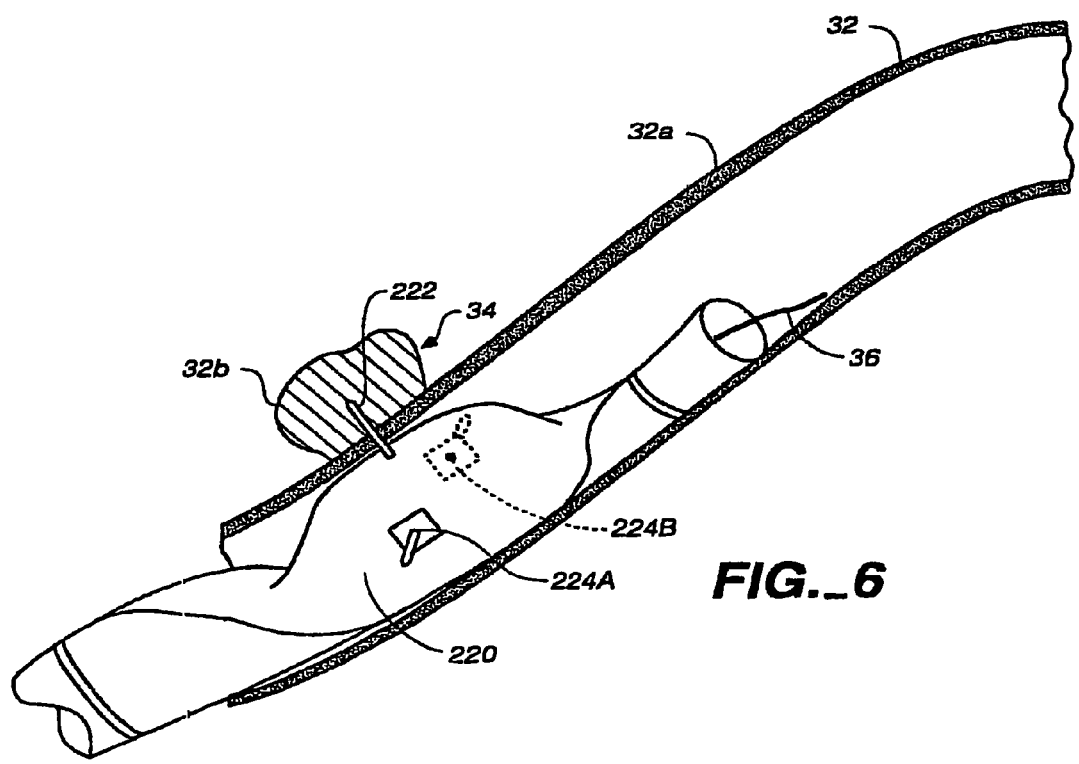
FIG._6

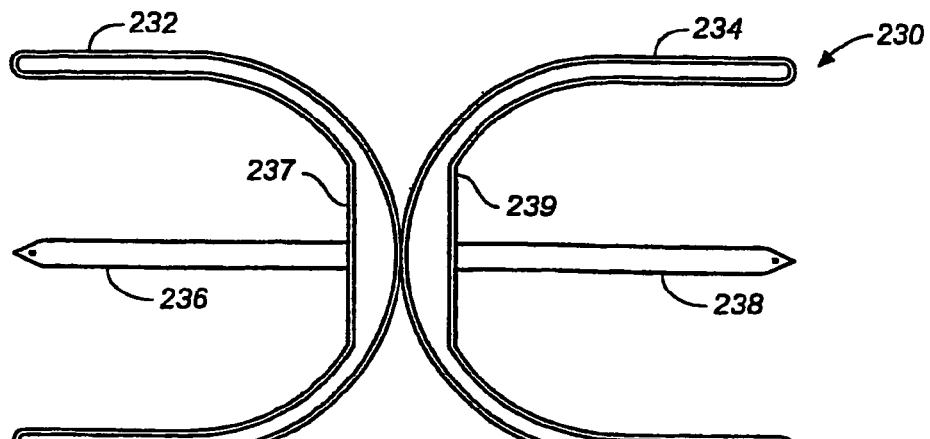
FIG._7A
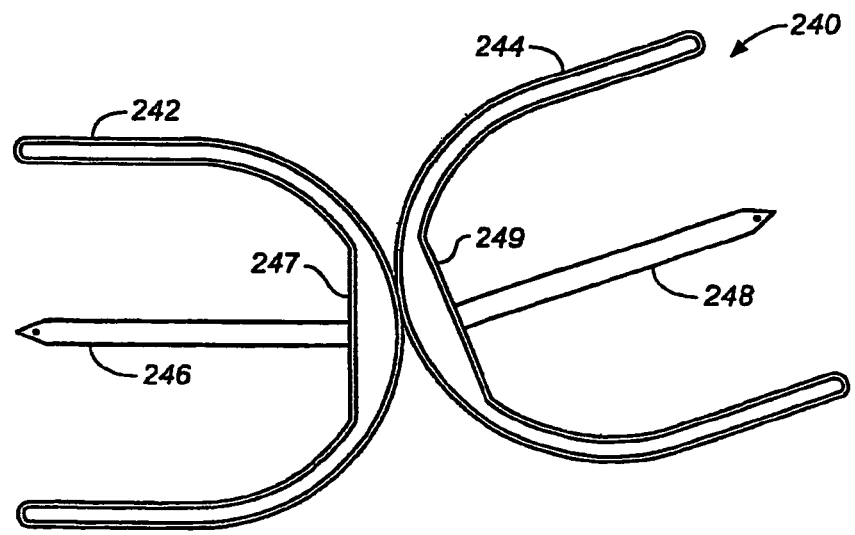
FIG._7B
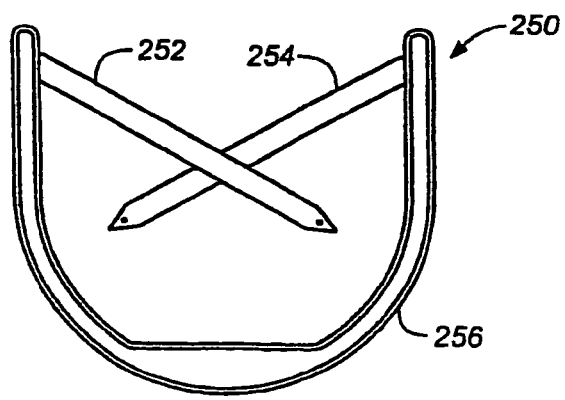
FIG._8

MICROFABRICATED SURGICAL DEVICE FOR INTERVENTIONAL PROCEDURES

This application is based on International Application No. PCT/US02/29666 filed on Sep. 20, 2002, which is a continuation-in-part of U.S. patent application Ser. No. 09/961,080 filed Sep. 20, 2001, now U.S. Pat. No. 6,547,803.

BACKGROUND

The present invention relates generally to surgical devices, and more particularly to microfabricated surgical devices for use in catheter-based interventional procedures.

Biological and surgical microelectromechanical systems (MEMS), useful for their ability to be placed into and easily maneuvered within a patient's body, are touted as the fastest growing area of micro-systems. For example, microcatheters are used in many medical applications for minimally invasive surgery. There are presently over one million surgical uses of catheters per year in the United States, representing a huge market.

As surgeons continue to adopt and perform advanced surgical procedures, the miniaturization of medical devices is taking place, allowing surgery with small external incisions and catheter-based microsurgical tools. With roots in laparoscopic surgery (entering the abdomen through the navel and small holes in the midsection), minimally invasive surgery can be performed by inserting catheters in the femoral artery at the base of a patient's thigh, navigating the blood vessels in the patient's body, and arriving at problem areas like the heart or brain. Once the distal tip of the catheter is precisely positioned inside the body, a microsurgical procedure like balloon angioplasty, stent placement, localized cauterization, or drug delivery can take place. With the reduced bodily reaction to microsurgery and the minimization of scar tissue, these procedures are highly preferred over more typical "macro" surgeries.

SUMMARY

In one aspect, the invention features an actuator for an interventional surgical procedure. The actuator comprises an actuator body having a distal end and a proximal end. A central expandable section is located between the distal end and the proximal end. The expandable section is operable between an unactuated condition in which the expandable section is in a furled state and an actuated condition in which the expandable section is in unfurled state. A needle at the expandable section is movable in an approximately perpendicular direction relative to a central longitudinal axis of the actuator body from a position within the actuator body to a position outside of the actuator body when the expandable section is caused to change from the furled state to the unfurled state.

Various implementations of the invention may include one or more of the following features. The proximal end of the actuator body may be joined to an end of a catheter. The distal end of the actuator body may be joined to a tip end of the catheter. The expandable section includes an interior open area and a delivery conduit is used to supply an activating fluid to the open area to cause the expandable section to change from the furled state to the unfurled state. The expandable section may be made from a polymer. The actuator may further include a retaining ring located at the distal end and at the proximal end of the actuator body. The needle may include a tip having an insertion edge or point. The tip may include an outlet port and a fluid pathway may be used to supply a therapeutic or diagnostic agent to the outlet port. The needle is a microfabricated needle, or it is a macroneedle.

In various embodiments, the needle may have a sharp, puncturing tip and a shaft. The shaft may have a longitudinal axis that extends substantially radially and substantially orthogonally relative to the longitudinal axis of the actuator when the expandable section is in an unfurled state. The sharp tip may be located radially away from an attachment point of the needle to the expandable section.

In another aspect, the invention is directed to a microfabricated surgical device for an interventional surgical procedure. The device includes a catheter having a distal end for insertion into and manipulation within a body of a vascularized organism and a proximal end for providing a user with control over the manipulation of the distal end of the catheter. An actuator is joined to the distal end of the catheter. The actuator includes an actuator body and a needle joined to an expandable section of the actuator body such that the needle is located within the actuator body when the actuator is in an unactuated condition and outside of the actuator body when the actuator is in an actuated condition. The needle is movable along a path substantially perpendicular to a central longitudinal axis of the actuator body when the actuator changes from the unactuated condition to the actuated condition. Fluid connections are provided at the distal end of the catheter and a proximal end of the actuator to supply a therapeutic or diagnostic agent to the needle, and to provide an activating fluid to the actuator to cause the actuator to change from the unactuated condition to the actuated condition.

Various implementations of the invention may include one or more of the following features. The catheter may be a therapeutic catheter. The expandable section may be in a furled state when the actuator is in the unactuated condition and in an unfurled state when the actuator is in the actuated condition. The expandable section may be made from a polymer. The device may further include a retaining ring located at opposite ends of the actuator body. The expandable section may include an interior open area to which the activating fluid is supplied to cause the expandable section to change from the furled state to the unfurled state. When the activating fluid is removed from the interior open area, the expandable section may return to the furled state.

In yet another aspect, the invention is directed to an actuator for an interventional surgical procedure comprising an actuator body having a distal end and a proximal end. A central expandable section is located between the distal end and the proximal end. The expandable section is operable between an unactuated condition in which the expandable section is in a furled state and an actuated condition in which the expandable section is in an unfurled state. A plurality of needles are located at the expandable section. The needles are movable in an approximately perpendicular direction relative to a central longitudinal axis of the actuator body from a position within the actuator body to a position outside of the actuator body, when the expandable section is caused to change from the furled state to the unfurled state.

Various implementations of the invention may include one or more of the following features. The needles may be spaced along a length of the expandable section. The plurality of needles move at the same time when the expandable section changes from the furled state to the unfurled state. At least one of the plurality of needles may move before another one of the plurality of needles when the expandable section changes from the furled state to the unfurled state. Also, when the expandable section changes from the furled state to the unfurled state, at least one of the plurality of needles may move in a direction that is different from the direction of movement of another one of the plurality of needles.

In still another aspect, the invention is directed to an actuator for an interventional surgical procedure comprising an actuator body having a distal end and a proximal end. An expandable section is located between the distal end and the proximal end. The expandable section is operable between a furled state and an unfurled state. A needle is located at the expandable section. The needle is movable from a position within the actuator body to a position outside of the actuator body, when the expandable section is caused to change from the furled state to the unfurled state.

An implementation of the invention may include a plurality of needles at the expandable section wherein when the expandable section changes from the furled state to the unfurled state, at least one of the needles moves in a direction that is different from the direction of movement of another one of the needles.

In yet another aspect, the invention is directed to an actuator for an interventional surgical procedure comprising an actuator body having a distal end and a proximal end. An expandable section is located between the distal end and the proximal end. The expandable section is operable between a furled state and an unfurled state. The actuator includes means for causing the expandable section to change from the furled state to the unfurled state. A needle is located at the expandable section, and the needle is movable in an approximately perpendicular direction relative to a central longitudinal axis of the actuator body from a position within the actuator body to a position outside of the actuator body, when the expandable section is caused to change from the furled state to the unfurled state.

An implementation of the invention may include means for delivering a therapeutic or diagnostic agent to the needle.

Intraluminal injection catheters according to the present invention comprise a catheter body and a needle. The needle is disposed radially within a protected recess of the catheter body, typically near a distal end of the catheter body. By "disposed radially," it is meant that the needle lies in a generally transverse direction perpendicular to the axis of the catheter body at the point where the needle is located. In this way, as the needle is extended in a radial direction from the protected recess, it will enter a luminal wall in a generally straight, radial direction which both maximizes the distance which the needle can penetrate into the luminal wall and which minimizes tearing or damage to the luminal tissue. In particular, the present prevention provides that the protected recess will have a depth which is greater than 60% of the width of the catheter body at the point where the needle is located, and further that the needle will have a length equal to at least 60% of the catheter body width at the location where the needle is located. Usually, the catheter body width will be a diameter for catheter bodies having circular cross-sections, but could also be a major or minor axes in catheter bodies having ovoid cross-sections or other widths in catheter bodies having other cross-sectional geometries.

Usually, the protected recess will be disposed within an expandable section of the catheter body, and the needle will be secured to an exterior surface of the expandable section. In that way, the needle will be radially advanced when the expandable section is radially expanded. In a presently preferred embodiment, the cross-section of the expandable section is initially involuted, when the expandable section is furled, with a generally circular outside, a generally circular protected recess, and an axial opening between the recess and the outside. The needle will be attached to the exterior surface of the catheter body within the protected recess at a location generally across from the axial opening so that the needle passes through the opening as the expandable section is unfurled.

The catheter bodies will usually have a length in the range from 50 cm to 250 cm, usually from 75 cm to 150 cm, with an outer diameter in the range from 1 mm to 5 mm, usually from 1.5 mm to 3 mm. The expandable section is typically expandable to maximum width in the range from 2 mm to 10 mm, usually from 3 mm to 8 mm. Typically, the expandable section will be expanded by receiving a pressurized activating fluid.

The present invention further provides an intraluminal catheter comprising a catheter body having a distal end, a proximal end, an exterior surface, and an expandable section located near the distal end and moveable between a furled configuration having a protected recess and an unfurled configuration. An effector, such as a needle, blade, sensor, electrode, or the like, is disposed on the exterior surface of the expandable section so that the effector is disposed within the protected recess when the expandable section is furled. The effector is advanced and usually filly exposed on the expandable section when the expandable section is unfurled. Usually, the catheter body has a generally circular exterior cross-section over at least most of its length, and the expandable section will have a similar circular exterior cross-section when furled. Other geometries as described above may also be used. The interior of the expandable section will typically be involuted when furled, preferably having a generally circular peripheral protected recess and an axial opening between the outside and the recess. When the effector comprise a needle, the needle will usually be attached to the exterior surface within the protected recess at a location generally across from the axial opening so that the needle passes through the opening as the expandable section is unfurled. The dimensions of the catheter body and nature of the expandable section are generally as described above with respect to the last embodiment.

An advantage of the invention is that it provides for highly-localized therapeutic or diagnostic agent deployments without significant risk to patients. The invention is able to generate a localized force that produces a microscale opening in the wall of an artery or vein without a significant axial motion component. This substantially eliminates the risk of tears to vessel walls. The invention produces a minute and self-healing wound. The invention permits, among other interventional procedures, localized tumor treatments and the treatment of in sclerotic arteries.

The details of one or more embodiments of the invention are set forth in the accompanying drawings and the description below. Other features, objects and advantages of the invention will be apparent from the description and drawings, and from the claims.

DESCRIPTION OF DRAWINGS

FIG. 1A is a schematic, perspective view of a microfabricated surgical device for interventional procedures in an unactuated condition.

FIG. 1B is a schematic view along line 1B-1B of FIG. A.

FIG. 1C is a schematic view along line 1C-1C of FIG. 1A.

FIG. 2A is a schematic, perspective view of a microfabricated surgical device for interventional procedures in an actuated condition.

FIG. 2B is a schematic view along line 2B-2B of FIG. 2A.

FIG. 3 is a schematic, perspective view of the microfabricated surgical device of the present invention inserted into a patient's vasculature.

FIGS. 4A-4G are schematic, perspective views illustrating steps in the fabrication of a microfabricated surgical device of the present invention.

FIG. 5 is a schematic, perspective view of another embodiment of the device of the present invention.

FIG. 6 is a schematic, perspective view of still another embodiment of the present invention, as inserted into a patient's vasculature.

FIGS. 7A and 7B are schematic views of other embodiments of the device of the present invention (in an unactuated condition) including multiple needles.

FIG. 8 is a schematic view of yet another embodiment of the device of the present invention (in an unactuated condition).

Like reference symbols and reference numbers in the various drawings indicate like elements.

DETAILED DESCRIPTION

The present invention is directed to microfabricated surgical devices and methods of using such devices in catheter-based interventional procedures. The present invention will be described in terms of several representative embodiments and processes in fabricating a microfabricated needle or microneedle, or even a macroneedle, for the interventional delivery of therapeutic or diagnostic agents into vascular walls or perivascular tissue. (A vascular wall is the wall of either an artery or vein). Exemplary therapeutic agents include: inorganic pharmacological agents; organic pharmacological agents; cells with special treatment functions including but not limited to undifferentiated, partially differentiated, or fully differentiated steam cells, islet cells, and genetically altered cells; micro-organisms including but not limited to viruses, bacteria, fungi, and parasites; organic genetic material including but not limited to genes, chromosomes, plasmids, DNA, RNA, mRNA, rRNA, tRNA, synthetic RNA, synthetic DNA, and combinations thereof; or any combination of the above listed agents. Exemplary diagnostic agents include: contrast mediums, radioactive makers, fluorescent makers, antibody makers, and enzyme makers.

The microneedle is inserted substantially normal to the wall of a vessel (artery or vein) to eliminate as much trauma to the patient as possible. Until the microneedle is at the site of an injection, it is positioned out of the way so that it does not scrape against arterial or venous walls with its tip. Specifically, the microneedle remains enclosed in the walls of an actuator or sheath attached to a catheter so that it will not injure the patient during intervention or the physician during handling. When the injection site is reached, movement of the actuator along the vessel terminated, and the actuator is operated to cause the microneedle to be thrust outwardly, substantially perpendicular to the central axis of a vessel, for instance, in which the catheter has been inserted As shown in FIGS. 1A-2B, a microfabricated surgical device 10 includes an actuator 12 having an actuator body 12a and a central longitudinal axis 12b. The actuator body more or less forms a C-shaped outline having an opening or slit 12d extending substantially along its length. In the illustrated embodiment, a single slit is provided. A microneedle 14 is located within the actuator body, as discussed in more detail below, when the actuator is in its unactuated condition (furled state) (FIG. 1B). The microneedle is moved fully outside the actuator body when the actuator is operated to be in its actuated condition (unfurled state) (FIG. 2B).

The actuator may be capped at its proximal end 12e and distal end 12f by a lead end 16 and a tip end 18, respectively, of a therapeutic catheter 20. The catheter tip end serves as a means of locating the actuator inside a blood vessel by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (μm), substantially rigid material, such as Parylene (types C, D or N), or a metal, for example, aluminum, stainless steel, gold, titanium or tungsten. The retaining rings form a rigid substantially "C"-shaped structure at each end of the actuator. The catheter may be joined to the retaining rings by, for example, a butt-weld, an ultra-sonic weld, integral polymer encapsulation or an adhesive such as an epoxy.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-rigid or rigid, expandable material, such as a polymer, for instance, Parylene (types C, D or N), silicone, polyurethane or polyimide. The central section 24, upon actuation, is expandable somewhat like a balloon-device.

The central section is capable of withstanding pressures of up to about 100 atmospheres upon application of the activating fluid to the open area 26. The material from which the central section is made of is rigid or semi-rigid in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube may be constructed of Teflon® or other inert plastics. The activating fluid may be a saline solution or a radio-opaque dye.

The microneedle 14 may be located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. Alternatively, the microneedle may be joined to the surface 24a by a metallic or polymer mesh-like structure 30 (See FIG. 4F), which is itself affixed to the surface 24a by an adhesive. The mesh-like structure may be made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a pharmaceutical or drug into a patient. The microneedle, however, does not need to be hollow, as it may be configured like a neural probe to accomplish other tasks.

As shown, the microneedle extends approximately perpendicularly from surface 24a. Thus, as described, the microneedle will move substantially perpendicularly to an axis of a vessel or artery into which has been inserted, to allow direct puncture or breach of vascular walls.

The microneedle further includes a pharmaceutical or drug supply conduit, tube or fluid pathway 14d which places the microneedle in fluid communication with the appropriate fluid interconnect at the catheter lead end. This supply tube may be formed integrally with the shaft 14b, or it may be formed as a separate piece that is later joined to the shaft by, for example, an adhesive such as an epoxy.

The needle 14 may be a 30-gauge, or smaller, steel needle. Alternatively, the microneedle may be microfabricated from polymers, other metals, metal alloys or semiconductor materials. The needle, for example, may be made of Parylene, silicon or glass. Microneedles and methods of fabrication are described in U.S. application Ser. No. 09/877,653, filed Jun. 8, 2001, entitled "Microfabricated Surgical Device", assigned to the assignee of the subject application, the entire disclosure of which is incorporated herein by reference.

The catheter 20, in use, is inserted through an artery or vein and moved within a patient's vasculature, for instance, a vein 32, until a specific, targeted region 34 is reached (see FIG. 3). As is well known in catheter-based interventional procedures, the catheter 20 may follow a guide wire 36 that has previously been inserted into the patient. Optionally, the catheter 20 may also follow the path of a previously-inserted guide catheter (not shown) that encompasses the guide wire. In either case, the actuator is hollow and has a low profile and fits over the guide wire.

During maneuvering of the catheter 20, well-known methods of fluoroscopy or magnetic resonance imaging (MRI) can be used to image the catheter and assist in positioning the actuator 12 and the microneedle 14 at the target region. As the catheter is guided inside the patient's body, the microneedle remains unfurled or held inside the actuator body so that no trauma is caused to the vascular walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12b of the actuator body 12a, to puncture a vascular wall 32a. It may take only between approximately 100 milliseconds and two seconds for the microneedle to move from its furled state to its unfurled state.

The ends of the actuator at the retaining rings 22a and 22b remain rigidly fixed to the catheter 20. Thus, they do not deform during actuation. Since the actuator begins as a furled structure, its so-called pregnant shape exists as an unstable buckling mode. This instability, upon actuation, produces a large scale motion of the microneedle approximately perpendicular to the central axis of the actuator body, causing a rapid puncture of the vascular wall without a large momentum transfer. As a result, a microscale opening is produced with very minimal damage to the surrounding tissue. Also, since the momentum transfer is relatively small, only a negligible bias force is required to hold the catheter and actuator in place during actuation and puncture.

The microneedle, in fact, travels so quickly and with such force that it can enter perivascular tissue 32b as well as vascular tissue. Additionally, since the actuator is "parked" or stopped prior to actuation, more precise placement and control over penetration of the vascular wall are obtained.

After actuation of the microneedle and delivery of the pharmaceutical to the target region via the microneedle, the activating fluid is exhausted from the open area 26 of the actuator, causing the expandable section 24 to return to its original, furled state. This also causes the microneedle to be withdrawn from the vascular wall. The microneedle, being withdrawn, is once again sheathed by the actuator.

As shown in FIG. 4A, the fabrication of the actuator 12 may start with a hollow tube or mandrel 36 that has a groove or slit 38 formed along part of its length. The tube or mandrel functions as a mold. It is coated with a dissolvable polymer that functions as a mold release device as discussed below. The wall thickness of the tube will define the cross-sectional dimension of the open area 26 of the actuator, and the exterior cross-sectional dimension of the tube will determine the exterior cross-sectional dimension of the actuator. The length of the tube, obviously, also determines the overall length of the actuator.

The retaining rings 22a and 22b are next placed at the opposite ends, respectively, of the tube (FIG. 4B). Specifically, they are slid over the exterior surface of the tube or into the interior surface of the tube. The tube and the retaining rings are then coated with a thin, rigid or semi-rigid, expandable material 40, such as Parylene, silicone, polyurethane or polyimide.

For instance, a Parylene C polymer may be gas vapor deposited onto and into the mold. Parylene is the trade name for the polymer poly-para-xylylene. Parylene C is the same monomer modified by the substitution of a chlorine atom for one of the aromatic hydrogens. Parylene C is used because of its conformality during deposition and its relatively high deposition rate, around 5 µm per hour.

The Parylene process is a conformal vapor deposition that takes place at room temperature. A solid dimer is first vaporized at about 150° C. and then cleaved into a monomer at about 650° C. This vaporized monomer is then brought into a room temperature deposition chamber, such as one available from Specialty Coating Systems of Indianapolis, Ind., where it condenses and polymerizes onto the mold. Because the mean free path of the monomer gas molecules is on the order of 0.1 centimeter (cm), the Parylene deposition is very conformal. The Parylene coating is pinhole free at below a 25 nanometer (nm) thickness.

Due to the extreme conformality of the deposition process, Parylene will coat both the inside (via the slit 38) and outside of the mold. The Parylene coating inside and outside the mold may be on the order of 5 to 50 µm thick, and more typically about 25 µm thick.

Other Parylenes, such as Types N and D, may be used in place of Parylene C. The important thing is that the polymer be conformally deposited. That is, the deposited polymer has a substantially constant thickness regardless of surface topologies or geometries.

Additionally, a fluid flood and air purge process could be used to form a conformal polymer layer on and in the mold. Also, a dip-coating process could be used to form a conformal polymer layer on and in the mold. Polymers that may be used in this process include polyurethane, an epoxy or a silicone.

As shown in FIG. 4C, the next step is to release the actuator structure 12 from the mold or tube 36. This is accomplished by virtue of the mold release. Specifically, the dissolvable polymer that was initially coated onto the tube is dissolved in a solvent to release the actuator structure from the mold. The actuator structure is then opened for placement of the microneedle 14 on the surface 24a of the expandable section 24 of the actuator (see FIG. 4D). Alternatively, if the expandable section 24 and the microneedle 14 are both made of Parylene, then the microneedle may be molded directly into surface 24a. A technique for such direct molding is described in the above-identified application Ser. No. 09/877,653, which has been incorporated herein by reference. Also, at this point, a suitable opening or passageway may be formed at the proximal end of the actuator for establishing fluid communication between the open area 26 of the actuator and the delivery conduit 28.

The microneedle is then placed in fluid communication with the proximal end of the actuator by means of, for instance, the pharmaceutical supply tube 14d (FIG. 4E). The microneedle and supply tube may be joined together by a butt-weld, an ultra-sonic weld or an adhesive such as an epoxy. The microneedle 14 is then adhered to surface 24a by, for example, the metallic mesh-like structure 30 described above. (FIG. 4F).

Next, as shown in FIG. 4G, the retaining ring 22b of the actuator is joined to the lead end of the catheter 20 by, for example, and as discussed, a butt-weld, an ultra sonic weld or an adhesive such as an epoxy. The tip end of the catheter is joined to the retaining ring 22a in a similar fashion or during actuator fabrication. At this point, the appropriate fluid interconnects can be made between the lead end of the catheter, and the distal tip of the microneedle and the open area 26 of the actuator.

Various microfabricated devices can be integrated into the needle, actuator and catheter for metering flows, capturing samples of biological tissue, and measuring pH. The device 10, for instance, could include electrical sensors for measuring the flow through the microneedle as well as the pH of the pharmaceutical being deployed. The device 10 could also include an intravascular ultrasonic sensor (IVUS) for locating vessel walls, and fiber optics, as is well known in the art, for viewing the target region. For such complete systems, high integrity electrical, mechanical and fluid connections are provided to transfer power, energy, and pharmaceuticals or biological agents with reliability.

By way of example, the microneedle may have an overall length of between about 200 and 3,000 microns (µm). The interior cross-sectional dimension of the shaft 14b and supply tube 14d may be on the order of 20 to 250 µm, while the tube's and shaft's exterior cross-sectional dimension may be between about 100 and 500 µm. The overall length of the actuator body may be between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls may have a length of about 4-40 mm, and a cross-sectional dimension of about 50-500 µm. The diameter of the delivery tube for the activating fluid may be about 100 µm. The catheter size may be between 1.5 and 15 French (Fr).

Variations of the invention include a multiple-buckling actuator with a single supply tube for the activating fluid. The multiple-buckling actuator includes multiple needles that can be inserted into or through a vessel wall for providing injection at different locations or times.

For instance, as shown in FIG. 5, the actuator 120 includes microneedles 140 and 142 located at different points along a length or longitudinal dimension of the central, expandable section 240. The operating pressure of the activating fluid is selected so that the microneedles move at the same time. Alternatively, the pressure of the activating fluid may be selected so that the microneedle 140 moves before the microneedle 142.

Specifically, the microneedle 140 is located at a portion of the expandable section 240 (lower activation pressure) that, for the same activating fluid pressure, will buckle outwardly before that portion of the expandable section (higher activation pressure) where the microneedle 142 is located. Thus, for example, if the operating pressure of the activating fluid within the open area of the expandable section 240 is two pounds per square inch (psi), the microneedle 140 will move before the microneedle 142. It is only when the operating pressure is increased to four psi, for instance, that the microneedle 142 will move. Thus, this mode of operation provides staged buckling with the microneedle 140 moving at time t1 and pressure p1, and the microneedle 142 moving at time t2 and p2, with t1 and p1 being less than t2 and p2, respectively.

This sort of staged buckling can also be provided with different pneumatic or hydraulic connections at different parts of the central section 240 in which each part includes an individual microneedle.

Also, as shown in FIG. 6, an actuator 220 could be constructed such that its needles 222 and 224A move in different directions. As shown, upon actuation, the needles move at angle of approximately 90° to each other to puncture different parts of a vessel wall. A needle 224B (as shown in phantom) could alternatively be arranged to move at angle of about 180° to the needle 224A.

Moreover, as shown in FIG. 7A, in another embodiment, an actuator 230 comprises actuator bodies 232 and 234 including needles 236 and 238, respectively, that move approximately horizontally at angle of about 180° to each other. Also, as shown in FIG. 7B, an actuator 240 comprises actuator bodies 242 and 244 including needles 246 and 248, respectively, that are configured to move at some angle relative to each other than 90° or 180°. The central expandable section of the actuator 230 is provided by central expandable sections 237 and 239 of the actuator bodies 232 and 234, respectively. Similarly, the central expandable section of the actuator 240 is provided by central expandable sections 247 and 249 of the actuator bodies 242 and 244, respectively.

Additionally, as shown in FIG. 8, an actuator 250 may be constructed that includes multiple needles 252 and 254 that move in different directions when the actuator is caused to change from the unactuated to the actuated condition. The needles 252 and 254, upon activation, do not move in a substantially perpendicular direction relative to the longitudinal axis of the actuator body 256.

Damage to the inside of arteries caused by abrasion or lesion can seriously affect patients with sometimes drastic consequences such as vasospasm, leading to arterial collapse and loss of blood flow. Breach of the arterial wall through interventional surgical needles can prevent such problems.

The use of catheter-based interventional surgical microneedles allows highly localized pharmaceutical injections without the limitation of injecting from outside the body. Common pharmaceutical procedures carried out with intravascular injections cause unnecessary flushing of the drugs throughout the body and filtering through the kidneys, liver and the lymphatic system. On the other hand, localized injections allow slow, thorough integration of the drug into the tissue, thus performing the task more efficiently and effectively, saving time, money, drugs, and lives.

A number of embodiments of the invention have been described. Nevertheless, it will be understood that various modifications may be made without departing from the spirit and scope of the invention.

What is claimed is:

1. An actuator for an interventional surgical procedure comprising:

an actuator body having a distal end and a proximal end, a central expandable section located between the distal end and the proximal end, said expandable section having an opening along its length and being operable between an unactuated condition in which said expandable section is in a furled state having an involute cross section and an actuated condition in which said expandable section is in an unfurled state, wherein the expandable section includes a protected recess having a depth greater than 60% of the width of the actuator body; and
a needle on said expandable section, said needle having a shaft and a sharp tip at an end of the shaft, and being movable in an approximately perpendicular direction relative to a central longitudinal axis of said actuator body from a position within said actuator body with the sharp tip positioned radially inward from the opening to a position outside of said actuator body when said expandable section is caused to change from said furled state to said unfurled state, wherein the needle shaft has a longitudinal axis that extends substantially radially and substantially orthogonally relative to the longitudinal axis of the actuator body when the expandable section is in an unfurled state, and wherein the sharp tip is located radially away from an attachment point of the needle to the expandable section of the actuator body, and wherein the needle is disposed radially within the protected recess and has a length equal to at least 60% of the width of the actuator body, and wherein the needle is fully extendable in a radial direction from the protected recess to penetrate a luminal wall when the actuator is in a body lumen, and wherein the needle tip includes an outlet port and the needle further includes a fluid delivery conduit suitable for delivering an agent to the outlet port to facilitate delivering the agent into a luminal wall when the actuator is in a body lumen.

2. The actuator of claim 1, wherein the proximal end is joined to an end of a catheter.

3. The actuator of claim 2, wherein the distal end is joined to a tip end of the catheter.

4. The actuator of claim 1, wherein said expandable section includes an interior open area and further including a delivery conduit to supply an activating fluid to the open area to cause said expandable section to change from said furled state to said unfurled state.

5. The actuator of claim 1, wherein said expandable section is made from a polymer.

6. The actuator of claim 1, further including a retaining ring located at the distal end and at the proximal end.

7. The actuator of claim 1, wherein the agent is a therapeutic agent selected from the group consisting of: an inorganic pharmacological agent; an organic pharmacological agent; a cell with a treatment function including an undifferentiated, partially differentiated, or fully differentiated stem cell, an islet, or a genetically altered cell; a micro-organism including a virus, a bacteria, a fungi, or a parasite; and an organic genetic material including a gene, a chromosome, a plasmid, DNA, RNA, mRNA, rRNA, tRNA, synthetic RNA, or synthetic DNA.

8. The actuator of claim 1, wherein the agent is a diagnostic agent selected from the group consisting of: a contrast medium, a radioactive marker, a fluorescent marker, an antibody marker, and an enzyme marker.

9. The actuator of claim 1, wherein the needle is a microfabricated needle.

10. The actuator of claim 1, wherein the needle is a macroneedle.

11. An actuator as in claim 1, wherein the expandable section has a single opening along its length.

12. An actuator as in claim 11, wherein the expandable section has a C-shaped cross-section with the shaft of the needle extending from across the expandable section in a direction toward the opening.

13. An actuator as recited in claim 1, wherein the sharp tip is a puncturing tip.

14. A microfabricated surgical device for an interventional surgical procedure comprising:
a catheter having a distal end for insertion into and manipulation within a body of a vascularized organism and a proximal end for providing a user with control over the manipulation of the distal end of the catheter within the body;
an actuator joined to the distal end of the catheter, said actuator including an actuator body including an expandable section having an opening along its length and a needle having a shaft and a sharp tip at and end of the shaft, and being attached to the expandable section of the actuator body such that said needle is located within said actuator body with the sharp tip positioned radially inward from the opening when said actuator is in an unactuated condition and fully outside of said actuator body when said actuator is in an actuated condition, said needle being movable along a path substantially perpendicular to a central longitudinal axis of said actuator body when said actuator changes from the unactuated condition to the actuated condition, wherein the needle shaft has a longitudinal axis that extends substantially radially and substantially orthogonally relative to the longitudinal axis of the actuator body when the expandable section is in the actuated condition, and wherein the sharp tip is a puncturing tip located radially away from an attachment point of the needle to the expandable section of the actuator body; and
fluid connections at the distal end of the catheter and a proximal end of said actuator to supply a therapeutic or diagnostic agent to said needle, and to provide an activating fluid to said actuator to cause said actuator to change from the unactuated condition to the actuated condition.

15. The device of claim 14, wherein the catheter is a therapeutic catheter.

16. The device of claim 14, wherein said expandable section is in a furled state when the actuator is in the unactuated condition and in an unfurled state when the actuator is in the actuated condition.

17. The device of claim 16, wherein said expandable section includes an interior open area to which the activating fluid is supplied to cause said expandable section to change from the furled state to the unfurled state.

18. The device of claim 17, wherein when the activating fluid is removed from the interior open area, said expandable section returns to the furled state.

19. The device of claim 14, wherein said expandable section is made from a polymer.

20. The device of claim 14, further including a retaining ring located at opposite ends of the actuator body.

21. An actuator as in claim 14, wherein the expandable section has a single opening along its length.

22. An actuator as in claim 14, wherein the expandable section has a C-shaped cross-section with a shaft of the needle extending from across the expandable section in a direction toward the opening.

23. A microfabricated surgical as recited in claim 14, wherein:
the expandable section includes a protected recess having a depth greater than 60% of the width of the actuator body;
the needle is disposed radially within the protected recess and has a length equal to at least 60% of the width of the actuator body;
the needle is fully extendable in a radial direction from the protected recess to penetrate a luminal wall when the actuator is in a body lumen; and the needle tip includes an outlet port and the needle further includes a fluid delivery conduit suitable for delivering an agent to the outlet port to facilitate delivering the agent into a luminal wall when the actuator is in a body lumen.

24. An actuator for an interventional surgical procedure comprising:
an actuator body having a distal end and a proximal end, a longitudinal axis and an expandable section located between the distal end and the proximal end, said expandable section having an opening along its length and being operable between a furled state having an involute cross section and an unfurled state, wherein the expandable section includes a protected recess having a depth greater than 60% of the width of the actuator body; and
a needle on said expandable section, said needle having a shaft and a sharp tip at an end of the shaft, and being movable from a position within said actuator body with the sharp tip positioned radially inward from the opening to a position outside of said actuator body, when said expandable section is caused to change from said furled state to said unfurled state, wherein the needle shaft has a longitudinal axis that extends substantially radially and substantially orthogonally relative to the longitudinal axis of the actuator body when the expandable section is in the unfurled state, and wherein the sharp tip is located radially away from an attachment point of the needle to the expandable section of the actuator body, and wherein the needle is disposed radially within the protected recess and has a length equal to at least 60% of the width of the actuator body, and wherein the needle is fully extendable in a radial direction from the protected recess to penetrate a luminal wall when the actuator is in a body lumen, and wherein the needle tip includes an outlet port and the needle further includes a fluid delivery conduit suitable for delivering an agent to the outlet port to facilitate delivering the agent into a luminal wall when the actuator is in a body lumen.

25. The actuator of claim 24, further including a second needle at said expandable section wherein when said expandable section changes from the furled state to the unfurled state, the second needle moves in a direction that is different from the direction of movement of the first needle.

26. An actuator as in claim 24, wherein the expandable section has a single opening along its length.

27. An actuator as in claim 24, wherein the expandable section has a C-shaped cross-section with the shaft of the needle extending from across the expandable section in a direction toward the opening.

28. An actuator for an interventional surgical procedure comprising:
an actuator body having a distal end and a proximal end, a longitudinal axis, and an expandable section located between the distal end and the proximal end, said expandable section having an opening along its length and being operable between a furled state having an involute cross section and an unfurled state, wherein the expandable section includes a protected recess having a depth greater than 60% of the width of the actuator body;
a fluid supply pathway suitable for delivering a fluid to the expandable section to facilitate causing said expandable section to change from said furled state to said unfurled state; and
a needle on said expandable section, said needle having a shaft and a sharp tip at an end of the shaft, and being movable in an approximately perpendicular direction relative to the longitudinal axis of said actuator body from a position within said actuator body with the sharp tip positioned radially inward from the opening to a position outside of said actuator body when said expandable section is caused to change from said furled state to unfurled statue, wherein the needle shaft has a longitudinal axis that extends substantially radially and substantially orthogonally relative to the longitudinal axis of the actuator body when the expandable section is in the unfurled state, and wherein the sharp tip is located radially away from an attachment point of the needle to the expandable section of the actuator body, and wherein the needle is disposed radially within the protected recess and has a length equal to at least 60% of the width of the actuator body and wherein the needle is fully extendable in a radial direction from the protected recess to penetrate a luminal wall when the actuator is in a body lumen and wherein the needle tip includes an outlet port and the needle further includes a fluid delivery conduit suitable for delivering an agent to the outlet port to facilitate delivering the agent into a luminal wall when the actuator is in a body lumen.

29. The actuator of claim 28, further including a second fluid supply pathway for delivering a therapeutic or diagnostic agent to said needle.

30. An actuator as in claim 28, wherein the expandable section has a single opening along its length.

31. An actuator as in claim 28, wherein the expandable section has a C-shaped cross-section with the shaft of the needle extending from across the expandable section in a direction toward the opening.

* * * * *